United States Patent [19]

Szpur

[11] 4,327,737
[45] May 4, 1982

[54] MEDICAL ELECTRODE ASSEMBLY

[76] Inventor: Roman Szpur, 2685 Culver Ave., Dayton, Ohio 45429

[21] Appl. No.: 150,207

[22] Filed: May 15, 1980

[51] Int. Cl.³ .............................................. A61B 5/04
[52] U.S. Cl. .................................... 128/640; 128/641
[58] Field of Search ............................ 128/639–641, 128/644, 783, 798, 802, 803

[56] References Cited

U.S. PATENT DOCUMENTS

| | | | |
|---|---|---|---|
| 3,685,645 | 8/1972 | Kawaguchi | 128/803 |
| 3,828,766 | 8/1974 | Krasnow | 128/641 |
| 3,945,384 | 3/1976 | Allison et al. | 128/641 |
| 3,977,392 | 8/1976 | Manley | 128/641 |
| 3,989,035 | 11/1976 | Zuehlsdorff | 128/641 |
| 4,034,854 | 7/1977 | Bevilacqua | 128/641 X |
| 4,102,331 | 7/1978 | Grayzel et al. | 128/640 |

*Primary Examiner*—Lee S. Cohen
*Attorney, Agent, or Firm*—Jacox & Meckstroth

[57] ABSTRACT

A flexible carrier sheet has an adhesive releasing outer surface and a heat-sealable inner surface, and one or more retaining pads are die-cut from a sheet or strip of breathable foam material attached to the outer surface by pressure-sensitive adhesive. Each retaining pad covers a hole cut within the carrier sheet and supports an electrical contact assembly which projects through the hole to confine an electrical conducting gel. A flexible bottom cover sheet has an air-impervious outer surface and a heat-sealable inner surface, and the edge or border portions of the carrier sheet and bottom cover sheet are heat-sealed together to form an air-tight chamber for the gel. The carrier sheet and bottom cover sheet may also be heat-sealed together in an area extending between adjacent electrodes, and the heat-sealed area may be provided with a line of weakening to provide for convenient separation of single electrode assemblies.

10 Claims, 4 Drawing Figures

MEDICAL ELECTRODE ASSEMBLY

BACKGROUND OF THE INVENTION

The medical electrode assembly of this invention relates to disposable medical electrodes of the type disclosed in applicant's U.S. Pat. No. 4,114,263 and in the other U.S. patents referred to therein. A plurality of such medical electrodes are normally carried by a carrier sheet or strip of coated paper and are peeled from the carrier sheet and applied to the skin of an individual or patient. Preferably, each electrode carries an electrically conductive gel which conducts a body generated voltage from the patient's skin to an electrical contact assembly which is connected by a flexible conductor to equipment for monitoring the patient or for producing an electrocardiogram for the patient.

In order to minimize the cost of producing such a disposable medical electrode, it has been found highly desirable for the electrode to be constructed in a manner which enables high volume production with simplicity and efficiency in manufacturing and which permits a plurality or group of electrodes to be simultaneously produced in progressive steps with a minimum of labor. In addition, it is important for the electrode to be constructed in a manner which assures a positive air-tight enclosure for the electrically conductive gel to provide for an extended "shelf-life" for the electrode.

SUMMARY OF THE INVENTION

The present invention is directed to an improved disposable medical electrode assembly which provides the desirable features mentioned above, and which particularly, is adapted to be economically and efficiently produced in high volume with the minimum of labor in order to minimize the cost of producing each electrode. The electrode assembly of the invention also assures an air-tight chamber for each electrode to avoid evaporation of the moisture within the electrical conducting gel.

In accordance with the illustrated embodiment of the invention, the above features and advantages are generally provided by adhesively attaching a retaining sheet of resilient porous foam material to a carrier sheet having an inner coating of plastics material and an outer coating of adhesive releasing silicone material. The retaining sheet is die cut down to the carrier sheet to form a retaining pad, and a circular hole is cut within the carrier sheet within the center of the pad. A circular inverted cup member is attached to the retaining pad by the adhesive on the bottom of the pad, and a snap-type electrical contact assembly extends through the cup member and the retaining pad.

A patch of resilient open cell foam material is confined within the cup member and carries an electrically conductive gel through which a D.C. current is passed to stabilize the gel with the contact assembly. The patch and gel are retained within the cup member by a bottom cover sheet having an inner coating of plastics material and an outer coating of silicone material. The inner coatings on the carrier sheet and on the bottom cover sheet are heat-sealed together outboard of the retaining pad and completely around the pad to form an air-tight enclosure or chamber for gel and patch.

Other features and advantages of the invention will be apparent from the following description, the accompanying drawing and the appended claims.

DESCRIPTION OF THE PREFERRED EMBODIMENTS

Figure 1:
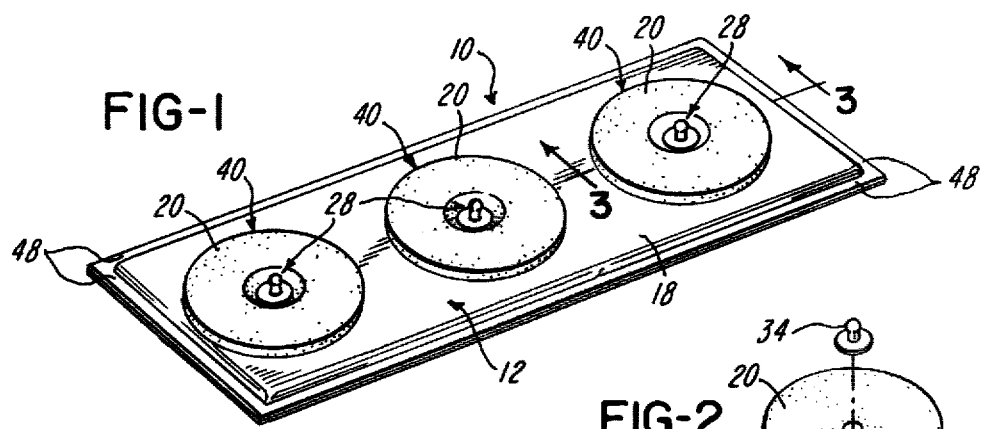
FIG. 1 is a perspective view of a medical electrode assembly constructed in accordance with the invention.
Figure 3:
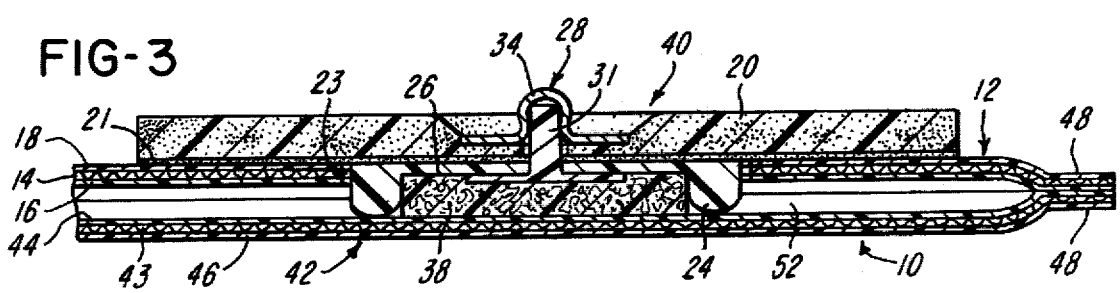
FIG. 3 is an enlarged fragmentary section of the medical electrode assembly as taken generally on the line 3—3 of FIG. 1.

FIG. 1 shows a medical electrode assembly 10 which includes a relatively stiff rectangular carrier sheet 12 formed by a paper sheet 14 (FIG. 3) having an inner coating 16 of plastics material such as polyethylene and an outer coating 18 of an adhesive releasing material such as a silicone material. In the manufacture of the electrode assembly 10, the carrier sheet 12 carries a rectangular strip of resilient breathable foam material such as polyvinylchloride foam, and the strip is die cut at longitudinally spaced intervals to form resilient retaining pads 20 which are attached to the carrier sheet 12 by corresponding layers of pressure-sensitive adhesive 21 (FIG. 3). After the die cutting operation, the matrix or skeleton of the foam material is peeled from the carrier sheet 12 so that only the pads 20 remain on the carrier sheet. While three circular pads 20 are illustrated in FIG. 1 on the carrier sheet 12, the electrode assembly 10 may be formed with one or more of the pads 20, and the pads may have a non-circular shape, if desired.

As shown in FIG. 3, a circular opening or hole 23 is cut within the carrier sheet 12 for each of the retaining pads 20, and each hole 23 is located concentrically with respect to the pad 20 which covers the hole. An inverted circular cup member 24 is located within each of the holes 23 and is secured to the corresponding retaining pad 20 by the layer of adhesive 21. Each of the cup members 24 is molded of a semi-flexible plastics material and defines a circular cavity 26. Preferably, each hole 23 is cut within the carrier sheet 12 while the foam sheet is being die-cut to form the corresponding pad 20.

An electrical snap-type contact assembly 28 is secured to the center portions of each retaining pad 20 and cup member 24, and includes an electrically conducting stud 31 which is preferably molded of a plastics material and coated with a silver plating in the same manner as described in above-mentioned U.S. Pat. No. 4,114,263. The stud 31 projects through aligned center holes within the cup member 24 and retaining pad 20 and receives a sheet metal snap element 34 which is formed from a metal such as silver, nickel or aluminum. The snap element 34 is pressed onto the tapered stud 31 and positively clamps the cup member 24 to the retaining pad 20.

A circular pad or patch 38 of resilient open-cell foam material is inserted into the cavity 26 of each cup member 24, and each patch 38 receives a predetermined quantity of electrically conductive gel. The gel-filled patch 38 cooperates with the cup member 24, retaining pad 20 and contact assembly 28 to form a medical electrode 40. As described in above-mentioned U.S. Pat. No. 4,114,263, a regulated DC current is passed through the contact assembly 28 of each electrode 40 to chlorodize the bottom surface of the stud 31 and to form a state of electrical rest between the gel and the stud 31.

The electrode assembly 10 also includes a rectangular bottom cover sheet 42 which is preferably formed of the same composite materials used in forming the carrier sheet 12. That is, the cover sheet 42 includes a paper sheet 43 having an upper or inner coating 44 of a thermoplastics material such as polyethylene and an outer coating 46 of a silicone material. The inner and outer coatings on the carrier sheet 12 and on the bottom cover sheet 42 result in making the sheets resistant to the absorption of moisture and also air-impervious.

Figure 2:
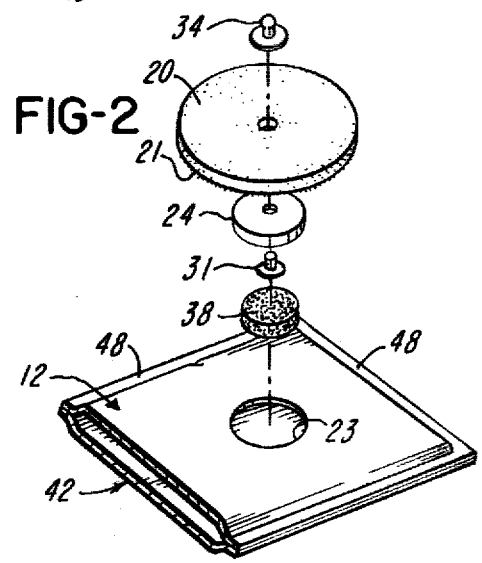
FIG. 2 is an exploded perspective view of a portion of the electrode assembly shown in FIG. 1.

As shown in FIGS. 1-3, the outer peripheral edge or border portions 48 of the carrier sheet 12 and bottom cover sheet 42 are secured or bonded together by a heat-sealing operation. During this operation, the overlapping edge portions 48 of the sheets are pressed together by heated bars or platens which are sufficiently hot to melt the inner coatings 16 and 44 of polyethylene and thereby fuse or bond the edge portions together around all of the medical electrodes 40 each of which is formed by a retaining pad 20, a cup member 24, a gel filled patch 38 and a conductor or contact assembly 28. The heat-sealed edge portions 48 are also effective to form an air-tight chamber 52 which encloses all of the cup members 24 and gel-filled resilient patches 38 so that the moisture within the gel does not evaporate, and the foam patches 38 remain effective for an extended period of time.

Figure 4:
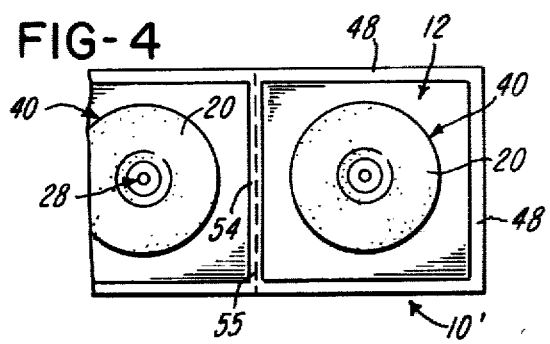
FIG. 4 is a fragmentary plan view of a modified electrode assembly constructed in accordance with the invention.

A modified electrode assembly 10' is illustrated in FIG. 4. The electrode assembly 10' is identical to the electrode assembly 10 described above. However, in the assembly 10', the carrier sheet 12 and the bottom cover sheet 42 are also heat-sealed together in between adjacent electrodes 40 along a laterally extending band or area 54. In addition, a line 55 of weakening in the form of a line of laterally spaced die cuts or perforations, extend through the sealed-together sheets 12 and 44 within the area 54. The line 55 of perforations enable each electrode 40 to be quickly and conveniently separated as a subassembly from each adjacent electrode without opening the corresponding air-tight chamber 52 for the electrode.

While the electrode assembly 10 may be efficiently manufactured in long strips, the electrodes 40 may be dispensed and/or used one-at-a-time, although the electrodes 40 may be packaged in groups or assemblies of three or more. When the individual or patient is ready to receive one or more electrodes, each electrode is removed from the carrier sheet 12 simply by peeling the resilient flexible pad 20 from the silicone coating 18 forming the outer surface of the carrier sheet. When the pad 20 is removed, it carries with it a cup member 24 and a gel filled foam patch 28 as a result of the attachment of the cup member 24 to the pad 20 by the adhesive 21 and the contact assembly 28.

As mentioned above, the construction of the electrode assembly 10 or 10' significantly simplifies the manufacturing of the medical electrode 40 in high volume. Since all of the manufacturing operations are adapted to be substantially automated, the production rate of electrodes per manufacturing individual or employee is significantly increased. The composition of the carrier sheet 12 and bottom cover sheet 42 also cooperate with the fused or heat-sealed border portions 48 to form a sealed air-tight chamber 52 for enclosing the gel-filled foam patches 58. Furthermore, while the particular form of medical electrode assembly 10 or 10' and the method of producing the assembly herein described constitute preferred embodiments of the invention, it is to be understood that the invention is not limited to these precise form and method, and that changes may be made therein without parting from the scope and spirit of the invention as defined in the appendant claims.

The invention having thus been described, the following is claimed:

1. A medical electrode assembly comprising a flexible carrier sheet having an adhesive releasing outer surface, an inner coating of heat sealable plastics material forming the inner surface of said carrier sheet, a retaining pad of flexible sheet material having a coating of adhesive on a surface thereof attached to said adhesive releasing outer surface of said carrier sheet, said carrier sheet having an opening covered by said retaining pad, electrical conducting means secured to said retaining pad and projecting through said opening, a flexible bottom cover sheet, an inner coating of heat sealable plastics material forming the inner surface of said bottom cover sheet, and said inner coating on said carrier sheet being heat-sealed to said inner coating on said bottom cover sheet in only an area surrounding said retaining pad and being unattached within said area to form an air-tight chamber larger than said retaining pad and enclosing said electrical conducting means.

2. An electrode assembly as defined in claim 1 wherein said carrier sheet and said bottom cover sheet each comprise a sheet of paper supporting the corresponding said inner coating of heat sealable plastics material.

3. An electrode assembly as defined in claim 2 and including a coating of silicon material on each of said paper carrier sheet and said paper cover sheet and forming the corresponding said outer surface of said carrier sheet.

4. An electrode assembly as defined in claim 1 wherein said carrier sheet and said cover sheet each has an outer coating of adhesive releasing material effective to restrict the passage of air and moisture through said sheets.

5. An electrode assembly as defined in claim 1 wherein said carrier sheet and said bottom cover sheet comprise the same sheet material.

6. An electrode assembly as defined in claim 1 wherein said carrier sheet and said bottom cover sheet are each elongated, said carrier sheet has a plurality of longitudinally spaced said openings, a corresponding plurality of longitudinally spaced said retaining pads attached to said carrier sheet, a corresponding plurality of said electrical conducting means secured to said retaining pads and projecting through said openings, and said carrier sheet and bottom cover sheet are heat-sealed together only outwardly of each of said retaining pads.

7. An electrode assembly as defined in claim 6 wherein said carrier sheet and said bottom cover sheet are also heat-sealed together in an area between adjacent said retaining pads to form a plurality of longitudinally disposed and individually sealed medical electrodes.

8. An electrode assembly as defined in claim 7 and including means forming a line of weakening disposed within said heat-sealed area between adjacent said retaining pads to provide for conveniently separating said electrodes while maintaining the air-tight chamber for each electrode.

9. A medical electrode assembly comprising an elongated flexible carrier sheet having an adhesive releasing outer surface, an inner coating of heat sealable plastics material forming the inner surface of said carrier sheet, a plurality of retaining pads of flexible sheet material, said pads having corresponding coatings of adhesive on a surface thereof attached to said adhesive releasing outer surface of said carrier sheet at longitudinally spaced intervals, said carrier sheet having a corresponding plurality of longitudinally spaced openings covered by said retaining pads, electrical conducting means secured to each said retaining pad and projecting through the corresponding said opening, an elongated flexible bottom cover sheet, an inner coating of heat sealable plastics material forming the inner surface of said bottom cover sheet, and said inner coating on said carrier sheet being heat-sealed to said inner coating on said bottom cover sheet in only an area surrounding all of said retaining pads and being unattached within said area to form an elongated air-tight chamber larger than all of said retaining pads and enclosing all of said electrical conducting means.

10. An electrode assembly as defined in claim 9 wherein said carrier sheet and said bottom cover sheet each comprise a paper sheet having the corresponding said inner coating of plastics material and an outer coating of adhesive releasing material for restricting the passage of air and moisture through said sheets.

* * * * *